(12) United States Patent
Kamada et al.

(10) Patent No.: US 9,039,936 B2
(45) Date of Patent: May 26, 2015

(54) THIOPHENE DERIVATIVE, METHOD FOR PRODUCING SAME, AND POLYMER OF THIOPHENE DERIVATIVE

(75) Inventors: Taisuke Kamada, Kurashiki (JP);
Toshio Fuchigami, Tokyo (JP);
Shinsuke Inagi, Tokyo (JP)

(73) Assignees: TOKYO INSTITUTE OF TECHNOLOGY, Tokyo (JP);
KURARAY CO., LTD., Okayama (JP)

( * ) Notice: Subject to any disclaimer, the term of this patent is extended or adjusted under 35 U.S.C. 154(b) by 485 days.

(21) Appl. No.: 13/386,492

(22) PCT Filed: Jul. 23, 2010

(86) PCT No.: PCT/JP2010/062418
§ 371 (c)(1),
(2), (4) Date: Jan. 23, 2012

(87) PCT Pub. No.: WO2011/010718
PCT Pub. Date: Jan. 27, 2011

(65) Prior Publication Data
US 2012/0119157 A1    May 17, 2012

(30) Foreign Application Priority Data

Jul. 24, 2009   (JP) .................................. 2009-173398

(51) Int. Cl.
| | | |
|---|---|---|
| H01B 1/12 | (2006.01) | |
| C07D 333/32 | (2006.01) | |
| C07D 495/04 | (2006.01) | |
| C08G 61/12 | (2006.01) | |

(52) U.S. Cl.
CPC ............ C07D 333/32 (2013.01); C07D 495/04 (2013.01); C08G 61/126 (2013.01); *C08G 2261/145* (2013.01); *C08G 2261/3223* (2013.01); *C08G 2261/514* (2013.01)

(58) Field of Classification Search
CPC .... H01B 1/127; C07D 333/04; C07D 333/46; C07D 339/00; C07D 339/02; C07D 339/08; C07D 495/02; C08G 75/00
USPC .................. 252/500; 528/377; 549/32, 35, 50
See application file for complete search history.

(56) References Cited

U.S. PATENT DOCUMENTS

| | | | | |
|---|---|---|---|---|
| 5,463,056 | A | * | 10/1995 | Jonas .............................. 544/350 |
| 7,118,692 | B2 | * | 10/2006 | Nordquist et al. ............ 252/500 |
| 7,262,264 | B2 | | 8/2007 | Werner et al. |
| 2004/0010115 | A1 | * | 1/2004 | Sotzing ......................... 528/377 |
| 2006/0155105 | A1 | | 7/2006 | Werner et al. |
| 2007/0172702 | A1 | * | 7/2007 | Elschner et al. .............. 428/690 |

FOREIGN PATENT DOCUMENTS

| | | | |
|---|---|---|---|
| EP | 1559739 | * | 8/2005 |
| EP | 1 810 986 A2 | | 7/2007 |
| JP | A-2010-62012 | | 3/2010 |
| WO | WO 2006/076156 A1 | | 7/2006 |
| WO | WO 2006/084088 A1 | | 8/2006 |
| WO | WO 2007/008978 A2 | | 1/2007 |

OTHER PUBLICATIONS

Neef et al "Synthesis and electronic properties of poly(2-phenylthieno[3,4-b]thiophene) . . . ", Chem. Mater. 1999, 11, 1957-1958.*
Pomerantz et al "Poly(2-decylthieno[3,4-b]thiophene) . . . " Synthetic Metals 84 (1997) 243-244.*
Jan. 22, 2013 European Search Report issued in Patent Application No. 10802338.3-2117.
Takeoka, Y. et al., "Self-assembled multilayer films based on functionalized poly(thiophene)s," *Synthetic Metals*, 2005, pp. 109-112, vol. 154.
Groenendaal, L. et al., "Electrochemistry of Poly(3,4-alkylenedioxythiophene) Derivatives," *Advanced Materials*, Jun. 5, 2003, pp. 855-879, vol. 15, No. 11.
International Search Report issued in International Application No. PCT/JP2010/062418 on Aug. 24, 2010 (with translation).

* cited by examiner

*Primary Examiner* — Mark Kopec
(74) *Attorney, Agent, or Firm* — Oliff PLC

(57) ABSTRACT

A novel polymer which has high solubility and good processability and is suitable as an electrically conductive material, and a novel compound which is a starting material of the polymer. The novel compound to be used as a starting material is a thiophene derivative represented by formula (I) shown below,

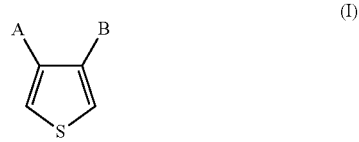

(I)

In the formula (I), A is S; and B is $R^2$ ($R^2$ is an alkylene group having a carbon number of 2 to 3 and optionally having a substituent), provided that A and B are intramolecularly cyclized to form, together with the thiophene group, a bicyclic heterocyclic structure. The novel polymer that is produced by polymerizing the thiophene derivative is suitable as an electrically conductive material.

4 Claims, No Drawings

THIOPHENE DERIVATIVE, METHOD FOR PRODUCING SAME, AND POLYMER OF THIOPHENE DERIVATIVE

TECHNICAL FIELD

The present invention relates to a novel compound with a thiophene skeleton, which can be utilized as an electrically conductive material and a method for producing the same, and to a novel polymer obtained from the novel compound with the thiophene skeleton.

BACKGROUND OF THE INVENTION

Polymers obtained through polymerization of a compound having a heteroatom-containing five-membered or aromatic-ring structure, such as pyrrole, thiophene, aniline, etc., is suitable as electrically conductive material, so that studies on the polymers are actively proceeding. Electric conductivity of these polymers can be freely controlled by changing the amount of a dopant, an ionic material, accordingly, practical application of these polymers to various electrodes, sensors, primary cells, secondary cells, solid electrolytic capacitors, antistatic agents, etc. has been attempted so far.

In particular, poly (3,4-alkylenedioxythiophene) derivatives are known as having a high conductivity, and various poly (3,4-alkylenedioxythiophene) derivatives have been reported (L. Groenendaal et al., Electrochemistry of Poly (3,4-alkylenedioxythiophene) Derivatives, Advanced Materials 2003, Vol. 15, No. 11, p. 855-879). However, solubility of the obtained poly (3,4-alkylenedioxythiophene) derivatives are not so high, so that there is somewhat difficulty in processability in film formation, accordingly improvement in solubility has been awaited.

SUMMARY OF THE INVENTION

The present invention was made to solve the problems mentioned above. An object of the present invention is to provide novel polymers which exhibits good solubility in solvent and processability and can be preferably used as electrically conductive materials, and to provide novel compounds that can be used as raw materials for the polymers.

Embodiment 1 of the present invention, which was made to solve the above-mentioned problems, is a thiophene derivative represented by formula (I) as shown below,

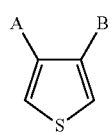

(I)

wherein in the formula (I): A is S, and B is $R^2$ ($R^2$ is an alkylene group having a carbon number of 2 to 3 and optionally having a substituent), and A and B are intramolecularly cyclized to form, together with the thiophene group, a bicyclic hetero ring structure (i.e. 2-ring heterocyclic structure); or A is $R^1$—O— ($R^1$ is an alkyl group having a carbon number of 1 to 10 and optionally having a substituent), and B is —$R^2$—SH ($R^2$ is an alkylene group having a carbon number of 2 to 3 and optionally having a substituent); or A is $R^1$—O— ($R^1$ is an alkyl group having a carbon number of 1 to 10 and optionally having a substituent), and B is —$R^2$—O—$SO_2$—$R^3$ ($R^2$ is an alkylene group having a carbon number of 2 to 3 and optionally having a substituent) and $R_3$ is a hydrocarbon group having a carbon number of 1 to 20 and optionally having a substituent).

Likewise, embodiment 2 of the present invention is a thiophene derivative having a bicyclic hetero ring structure according to embodiment 1, wherein, in said formula (I); A is S, and B is $R^2$ ($R^2$ is an alkylene group having a carbon number of 2 to 3 and optionally having a substituent), the thiophene derivative being represented by the formula (II) shown below.

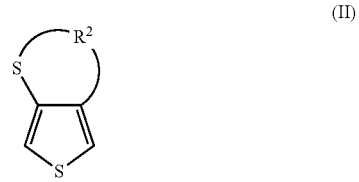

(II)

Likewise, embodiment 3 of the present invention is a thiophene derivative according to embodiment 1, wherein, in said formula (I); A is $R^1$—O— ($R^1$ is an alkyl group having a carbon number of 1 to 10 and optionally having a substituent), and B is —$R^2$—SH ($R^2$ is an alkylene group having a carbon number of 2 to 3 and optionally having a substituent); the thiophene derivative being represented by the formula (III) shown below.

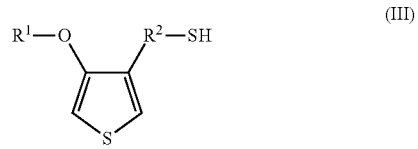

(III)

Embodiment 4 of the present invention is a thiophene derivative as described in embodiment 1 wherein, in said formula (I), A is $R^1$—O— ($R^1$ is an alkyl group having a carbon number of 1 to 10 and optionally having a substituent), B is —$R^2$—O—$SO_2$—$R^3$ ($R^2$ is alkylene group having a carbon number of 2 to 3 and optionally having a substituent, and $R^3$ is a hydrocarbon group having a carbon number of 1 to 20 and optionally having a substituent); the thiophene derivative being represented by the formula (IV) shown below.

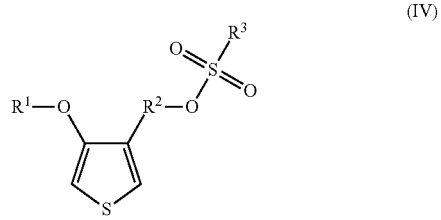

(IV)

Embodiment 5 of the present invention, which was made to solve the above mentioned problems, is a polymer having a constitutional unit of bicyclic hetero ring skeleton represented by a formula (V) shown below,

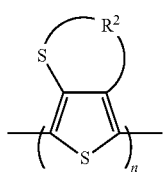

(V)

(in the formula (V), $R^2$ is an alkylene group having a carbon number of 2 to 3 and optionally having a substituent, and n is an integer of 2 or more).

Likewise, embodiment 6 of the present invention, which was made to solve the above mentioned problems is a composition comprising a polymer having the constitutional unit represented by said formula (V) and a dopant.

Embodiment 7 of the present invention, which was made to solve the above mentioned problems is a method for producing a thiophene derivative having a bicyclic hetero ring structure represented by said formula (II), which comprises a step of subjecting the thiophene derivative represented by said formula (III) to intramolecular cyclization reaction.

Likewise, embodiment 8 of the present invention is a method for producing a thiophene derivative represented by said formula (IV), which comprises a step of getting a compound represented by a formula (VI) shown below to react with Cl—$SO_2$—$R^3$ ($R^3$ is a hydrocarbon group having a carbon number of 1 to 20 and optionally having a substituent),

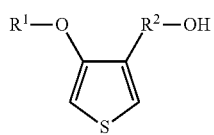

(VI)

(in the formula (VI), $R^1$ is an alkyl group having a carbon number of 1 to 10 and optionally having a substituent, and $R^2$ is an alkylene group having a carbon number of 2 to 3 and optionally having a substituent).

Likewise, embodiment 9 of the present invention is a method for producing a thiophene derivative represented by said formula (III), which comprises steps of: getting the thiophene derivative represented by said chemical formula (IV) to react with thiourea to produce a reaction product; and then hydrolyzing the reaction product.

According to the production method described in embodiment 8, the thiophene derivative, a novel compound represented by said formula (IV) in embodiment 4, can be obtained, and the novel compound is used as a starting compound of the thiophene derivative represented by said formula (III). According to the production method described in embodiment 9, the thiophene derivative represented by said formula (III), which is the invention described in embodiment 3, is produced from the thiophene derivative (IV), a novel compound. The thiophene derivative (III) is a starting compound for producing a novel thiophene derivative having the bicyclic hetero ring structure. The bicyclic hetero ring structure represented by said formula (II) is produced from the thiophene derivative (III) using the invention described in embodiment 7.

The polymer represented by formula (V) which is the invention described in embodiment 5, is a novel polymer obtained by polymerizing the thiophene derivative (II) which is a novel compound; is used as a conductive material; and exhibits high solubility and excellent processability. This thiophene derivative polymer (V) is blended with a dopant to constitute a composition, which is the invention described in embodiment 6 and is used, after electric conductivity is adjusted, for various electrodes, sensors, primary cells, secondary cells, solid electrolytic capacitors, antistatic agents, etc.

The present invention is made to provide a thiophene derivative comprehensively represented by said chemical formula (I), more specifically, to provide a thiophene derivative represented by said formula (II), a thiophene derivative represented by said formula (III) and a thiophene derivative represented by said formula (IV). Further, the present invention is made to provide a polymer represented by said formula (V) which has a constitutional unit of the thiophene derivative represented by said formula (II), and to provide a composition comprising this polymer and a dopant.

The number average molecular weight (Mn) of the polymer represented by the formula (V) is in the range of 200 to 1,000,000, and the weight average molecular weight (Mw) is in the range of 200 to 1,000,000.

In the formulas (I), (III), (IV) and (VI), $R^1$ is an alkyl group having a carbon number of 1 to 10 and optionally having a substituent, and the alkyl group can be a linear or branched chain. As the alkyl group, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group, etc. can be exemplified.

Considering a chemical reaction rate at the time of intramolecular cyclization reaction, which will be described later, this $R^1$ is preferably an alkyl group having a carbon number of 1 to 4 and optionally having a substituent. More specifically, methyl group, ethyl group, n-propyl group and n-butyl group are preferably used as the alkyl group.

In said formulas (I) to (VI), $R^2$ is an alkylene group having a carbon number of 2 to 3 and optionally having a substituent, and as alkylene group, 1,2-ethylene group, 1,2-propylene group or 1,3-propylene group is used.

In said formulas (I) and (IV), $R^3$ is a hydrocarbon group having a carbon number of 1 to 20 and optionally having a substituent. For example, an alkyl group optionally having a substituent, an alkenyl group optionally having a substituent, an aryl group optionally having a substituent, etc. can be exemplified.

The alkyl group in $R^3$ optionally having a substituent may be a linear or branched chain. As the alkyl group, for example, methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group, etc. can be exemplified.

The alkenyl group optionally having a substituent may be a linear or branched chain. As the alkenyl group, for example, vinyl group, allyl group, methylvinyl group, propenyl group, butenyl group, pentenyl group, hexenyl group, cyclopropenyl group, cyclobutenyl group, cyclopentenyl group, cyclohexenyl group, can be exemplified.

As an aryl group optionally having a substituent, for example, phenyl group, naphthyl group, anthryl group, phenanthryl group, p-tolyl group, etc. are exemplified.

The dopant serves as a counter anion to the polymer having an oxidized and positively-charged constitutional unit represented by formula (V). As specific examples, a halogenated anion of the group 5B elements such as $PF_6^-$, $S_bF_6^-$, $A_sF_6^-$, etc., a halogenated anion of the 3B group elements such as $BF_4^-$, etc., a halogen anion such as $I^-$ ($I_3^-$), $Br^-$, $Cl^-$, etc., a halogen acid anion such as $ClO_4^-$, etc., a metallic halide anion such as $AlCl_4^-$, $FeCl_4^-$, $SnCl_5^-$, etc., a nitrate anion represented by $NO_3^-$, a sulfate anion represented by $SO_4^{2-}$, an organic sulfonic acid anion such as p-toluene sulfonic acid anion, naphthalene sulfonic acid anion, $CH_3SO_3^-$, $CF_3SO_3^-$, etc., a carboxylic acid anion such as $CF_3COO^-$, $C_6H_5COO^-$, etc., and a modified polymer, etc. having an above-mentioned anion species in its main chain or side chain. Such anion species can be used alone or in combination of two or more. An adding method of such anions is not specifically limited. However, for example, a desired anion can be arbitrarily added after polymerization. In the case where polymerization is carried out using a chemical oxidative polymerization, an anion derived from an oxidant used can be used as it is. Further, in the case where polymerization is carried out using an electropolymerization, an anion derived from an electrolyte can be used as it is.

In the present invention, the thiophene derivative represented by the formula (IV) is preferably produced by a reaction process (X), as shown in reaction equation (X), in which a compound represented by formula (VI) is reacted with an organic sulfonyl chloride represented by formula (VII) to produce a sulfonate.

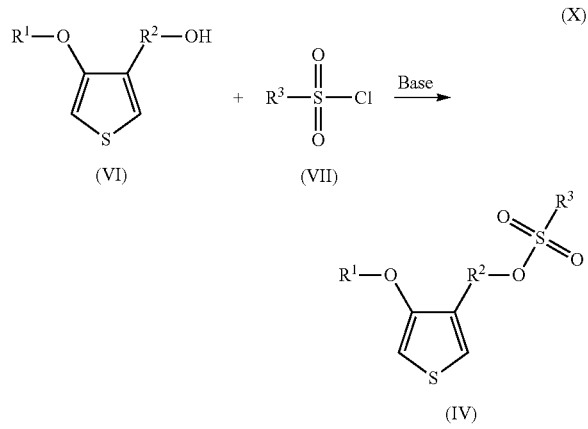

In equation (X), $R^1$, $R^2$ and $R^3$ are the same as described in said formulas (IV) and (VI).

As a preferred embodiment of the reaction Process (X), an organic sulfonic acid chloride (VII) is added dropwise into a solution including the compound (VI) and a base to induce a chemical reaction under an inactive gas environment such as, for example, nitrogen or argon.

The reaction process (X) is carried out preferably in the presence of solvent. As such solvent, for example, a saturated aliphatic hydrocarbon such as pentane, hexane, heptane, octane, nonane, decane, cyclohexane, etc., an aromatic hydrocarbone such as benzene, toluene, ethyl benzene, propyl benzene, xylene, ethyl toluene, etc., an ether such as diethylether, tetrahydrofuran, diisopropyl ether, dioxane, dimethoxyethane, dibutylether, etc.; a nitrile such as acetonitrile, propionitrile, benzonitrile, etc.; methylene chloride, chloroform, carbon tetrachloride, 1,2-dichloroethane, 1,1-dichloroethane, trichloroethane, chlorobenzene, etc., can be exemplified. Among them, a halogen-base solvent, specifically methylene chloride, is preferably used. These solvents can be used alone or in combination of two or more. The amount of such solvent to be used is preferably in the range of 1 to 100 parts by mass per 1 part by mass of the composition (VI).

The organic sulfonic acid chloride (VII) used in chemical reaction process (X) is not specifically limited. As $R^3$ in the organic sulfonic acid chloride (VII) or a hydrocarbon group having a carbon number of 1 to 20 and optionally having a substitute, a linear or branched alkyl group having a carbon number of 1 to 20 such as methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, isohexyl group, 2-ethylhexyl group, n-heptyl group, n-octyl group, n-nonyl group, n-decyl group, etc.; a linear or branched alkenyl group having a carbon number of 2 to 20 such as vinyl group, allyl group, methylvinyl group, propenyl group, butenyl group, pentenyl group, hexenyl group, cyclopropenyl group, cyclobutenyl group, cyclopentenyl group, cyclohexenyl group, etc.; and an aryl group such as a phenyl group, naphthyl group, anthryl group, phenanthryl group, p-tolyl group, etc.: are exemplified.

Among them, given the reaction temperature, processability, cost of catalyzer, etc., at least one of the acid selected from a group consisting of methanesulfonic acid chloride and p-toluene sulfonic acid chloride is preferably used. The amount used of such an acid is preferably in the range of 1 to 20, more preferably 1.0 to 4.0 equivalents per thiophene derivative represented by formula (V).

A base used in the reaction process (X) is not specifically limited, but an organic base such as N-methylmorphorine, triethylamine, tributylamine, diisopropylethyl amine, dicyclohexyl amine, N-methyl piperidine, pyridine, 4-pyrrolidinopyridine, picoline, 4-(N,N-dimethylamino)pyridine, 2,6-di-(tert-butyl)-4-methyl pyridine, quinoline, N,N-dimethyl aniline, N,N-diethylaniline, etc., are used but pyridine is preferably used. The amount used of such a base is preferably in the range of 1 to 20, more preferably 1.0 to 4.0 equivalents per thiophene derivative represented by the formula (V).

In the reaction process (X), the reaction temperature at the time of sulfonic acid esterification is not specifically limited, but a preferred temperature is in the range of −40 to 150° C. When the reaction temperature is lower than −40° C., the reaction rate could become extremely low, so that the temperature is preferably not lower than −20° C. On the contrary, when the temperature exceeds 100° C., degradation of the product material might be enhanced, so that the temperature is preferably controlled so as not to exceed 100° C. The reaction time is ordinary 1 to 30 hours, and the reaction pressure is ordinary in the range of from atmospheric pressure to 3 Mpa (gauge pressure).

After the solvent was distilled away from the reaction mixture obtained through the reaction process (X), the thiophene derivative was then purified by recrystallization and column chromatography, thereby obtaining a highly-purified thiophene derivative represented by the formula (IV).

Next, the thiophene derivative represented by the formula (IV) obtained from the above mentioned reaction process (X) is used as a starting compound and is reacted with thiourea, as shown in a reaction process (XI) in the chemical reaction equation (XI) described below. The product obtained is then hydrolyzed in the presence of a base, producing a thiophene derivative represented by the formula (III).

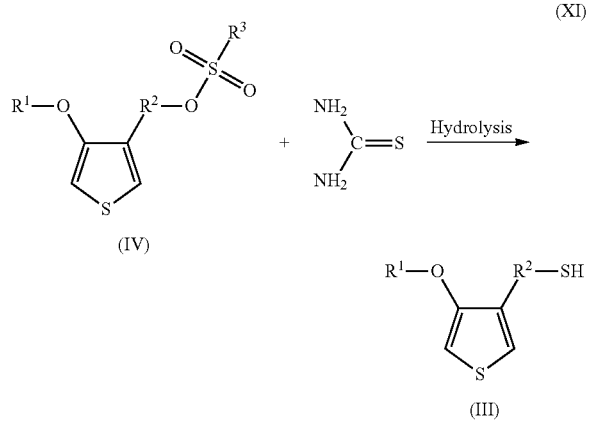

In the chemical equation (XI), $R^1$, $R^2$ and $R^3$ are the same as described in said formulas (III) and (IV).

As a preferred embodiment of the reaction process (XI), for example, the compound (IV) and thiourea react with each other in the presence of a solvent under an environment of an inactive gas such as nitrogen or argon, and then reaction product is subjected to hydrolysis.

The reaction with thiourea in the reaction process (XI) is preferably carried out in the presence of solvent. As such solvent, for example, methanol, ethanol, normal propanol, isopropanol, water can be exemplified. Among them, preferred solvent is a combination of alcoholic solvent and water, and combination of 3 kinds of solvent can also be used. The preferred amount of solvent used in the reaction is in the range of 1 to 100 parts by mass per 1 part by mass of the compound (IV).

In the reaction process (XI), the reaction temperature at the time of reacting with thiourea is not specifically limited, but the reaction is carried out preferably at the range of from 0° C. to 150° C. When the reaction temperature is less than 0° C., the reaction rate extremely decreases. Preferred reaction temperature is 20° C. or higher. On the other hand, when the reaction temperature exceeds 150° C., degradation of the product might be enhanced, so that the temperature is preferably controlled so as not to exceed 120° C. The reaction time is ordinary 1 to 30 hours, and the reaction pressure is ordinary in the range of from atmospheric pressure to 3 Mpa (gauge pressure).

A base used for the hydrolysis in the reaction process (XI) is not specifically limited, but a metallic hydroxide such as sodium hydroxide, potassium hydroxide, etc., a metallic carbonate such as sodium carbonate, potassium carbonate, etc., a metal alcoholate such as sodium methylate, sodium ethylate, potassium tert-butylate, etc., can be exemplified. Among them, given the reaction temperature, processability, cost of catalyzer, etc., at least one of the base selected from a group consisting of sodium hydroxide and potassium hydroxide is preferably used. The amount used of such a base is preferably in the range of 1 to 20, more preferably 1.0 to 4.0 equivalents per thiophene derivative represented by the formula (IV).

In the reaction process (XI), the reaction temperature at the time of hydrolysis is not specifically limited, but preferably is in the range of −20° C. to 100° C. When the reaction temperature is lower than −20° C., the reaction rate may become extremely low, so that the temperature is preferably not lower than 0° C. On the contrary, when the temperature exceeds 100° C., degradation of the product material might be enhanced, so that the temperature is more preferably con-trolled so as not to exceed 80° C. The reaction time is ordinary 1 to 30 hours, and the reaction pressure is ordinary in the range of from atmospheric pressure to 3 Mpa (gauge pressure).

From the reaction mixture obtained through the reaction process (XI), solvent was distilled away, and then mixture is purified by recrystallization and column chromatography, thereby obtaining a highly-purified thiophene derivative represented by the formula (III).

Next, the thiophene derivative which is represented by the formula (III) and is obtained from the above mentioned reaction process (XI), is subjected, as a starting compound, to an intramolecular cyclization reaction in a reaction process (XII) shown by the following chemical reaction equation (XII), to obtain the thiophene derivative represented by the formula (II).

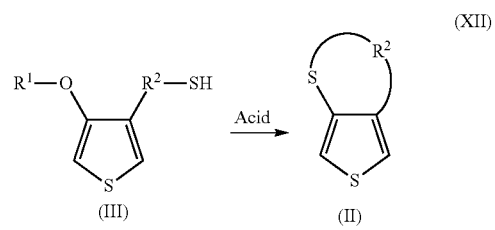

In the chemical equation (XII), R' and $R^2$ are the same as described in said formulas (II) and (III).

As a preferred embodiment of the reaction process (XII), for example, a process in which the thiophene derivative represented by the formula (III) is subjected to a chemical reaction in the presence of solvent and acid under an inactive gas environment such as nitrogen or argon; is exemplified.

The reaction process (XII) is preferably carried out in the presence of solvent. As such solvent, for example, a saturated aliphatic hydrocarbon such as pentane, hexane, heptane, octane, nonane, decane, cyclohexane, etc.; an aromatic hydrocarbon such as benzene, toluene, ethylbenzene, propylbenzene, xylene, ethyltoluene, etc.; an ether such as diethylether, tetrahydrofuran, diisopropylether, dioxane, dimethoxyethane, dibutylether, etc.; a nitrile such as acetonitrile, propionitrile, benzonitrile, etc.; methylene chloride, chloroform, carbon tetrachloride, 1,2-dichloroethane, 1,1-dichloroethane, trichloroethane, chlorobenzene, etc.: can be exemplified.

Among them, aromatic hydrocarbons are preferably used, specifically, toluene and xylene are preferably used. These solvents can be used alone or in combination of two or more. Preferred amount of solvent to be used is in the range of 1 to 100 parts by mass per 1 part by mass of the compound (III).

An acid used in the reaction process (XI) is not specifically limited, but for example, an inorganic acid or its salt such as hydrochloric acid, sulfuric acid, phosphoric acid, polyphosphoric acid, sodium hydrogensulfate, potassium hydrogensulfate, potassium dihydrogenphosphate, sodium hydrogen sulfite, potassium hydrogen sulfite, phosphotungstic acid, phosphomolybdic acid, silicotungstic acid, silicomolybdic acid, etc.; a sulfonic acid such as methane sulfonic acid, benzene sulfonic acid, p-toluene sulfonic acid, etc.; a carbonic acid such as acetic acid, propionic acid, benzoic acid, terephthalic acid, etc.; a solid acid such as silica, alumina, silica-alumina, titania, silica-titania, niobium oxide, etc.; an acidic ion-exchange resin such as sulfonic acid-base ion-exchange resin, carbonic acid-base ion-exchange resin, etc.; can be exemplified.

Among them, given the reaction temperature, processability, cost of catalyzer, etc., at least one of the acid selected from a group consisting of an inorganic base or its salt and sulfonic acid can be preferably used. Specifically, at least one of the acid selected from a group consisting of potassium hydrogensulfate, sodium hydrogensulfate and p-toluene sulfonic acid can be preferably used. Preferred amount of such acid to be used is, given the efficiency of the reaction, in the range of 0.001 to 100, more preferably 0.1 to 50 percent by mole per thiophene derivative represented by the formula (III).

In the reaction process (XII), the temperature at the time of the intramolecular cyclization reaction is not specifically limited, but the preferred temperature is in the range of from 0 to 150° C. When the reaction temperature is lower than 0° C., the reaction rate may become extremely low, so that the temperature is preferably set at 20° C. or higher. On the contrary, when the temperature exceeds 150° C., degradation of the reaction product might be enhanced, so that the temperature is preferably controlled so as not to exceed 120° C. The reaction time is ordinary 1 to 30 hours, and the reaction pressure is ordinary in the range of from the atmospheric pressure to 3 Mpa (gauge pressure).

Solvent was distilled away from the final reaction mixture obtained through the reaction process (XII), the obtained residue material can be used as it is for polymerization reaction. However, if needed, the obtained residue material may be purified by recrystallization and column chromatography, thereby obtaining a highly-purified thiophene derivative represented by the chemical formula (II).

Next, the thiophene derivative represented by the formula (II) obtained through the reaction process (XII) is used to produce the polymer represented by the formula (V) as described in the reaction process (XIII) shown by the following chemical equation (XIII).

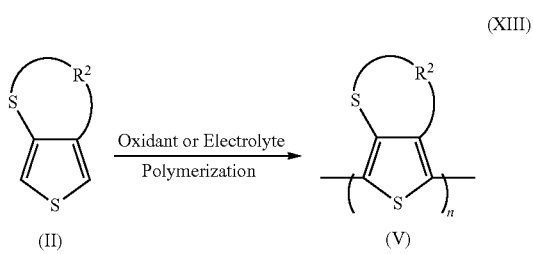

(XIII)

The polymer represented by the formula (V) shows a neutral state. A structure that exhibits conductive property is achieved by a composition comprising; the polymer represented by the formula (V) which is oxidized and electrically charged; and a dopant which serves as a counter anion.

The polymer represented by the formula (V) shows a Head-to-Tail configuration, but the polymer of the present invention is not limited to, and may include Tail-to-Tail and Head-to-Head configurations, too.

Polymerization reaction of the reaction process (XIII) is not specifically limited, but a chemical oxidative polymerization and electropolymerization are a preferred polymerization reaction. Among the chemical oxidative polymerization, a method in which the polymer is obtained through dehydrogenation of the monomer compound using an oxidant, is preferably adopted.

The polymer in the neutral state represented by said formula (V) can be obtained by reducing, using an alkaline solution such as ammonia, hydrazine, etc., a composite (composition) comprising a polymer which is represented by the formula (V) having a positive charge and a dopant which serves as a counter anion.

An oxidant used in the chemical oxidative polymerization is not specifically limited, but preferred oxidant is a transition metal salt. As the transition metal salt, for example, ferric salts such as ferric chloride ($FeCl_3$), ferric perchlorate ($Fe(ClO_4)_3$), ferric sulfate ($Fe_2(SO_4)_3$), an alkoxybenzene sulfonic acid iron having a carbon number of 1 to 16, alkylbenzene sulfonic acid iron having a carbon number of 1 to 16, naphthalene sulfonic acid iron, phenol sulfonic acid iron, sulfoisophthalic acid dialkylester iron, alkylsulfonic acid iron, alkoxynaphthalene sulfonic acid iron, tetralin sulfonic acid iron, etc., and cerium (IV) salts, copper (II) salts, manganese (VII) salts, ruthenium salts (III) can be used instead of iron (III) salts of said compound mentioned above. Among them, iron (III) salts can be preferably used.

In the reaction process (XII), in the case where polymerization is carried out using electropolymerization method, an electrolysis solution which contains a monomer, a raw material for the polymerizarion, is prepared. Then a voltage is applied between electrodes that are disposed apart from each other via the electrolysis solution, thereby producing an anodically-oxidized polymer on the anode.

As a solvent used in the electrolysis solution, nitromethane, acetonitrile, propylene carbonate, nitrobenzene, cyanobenzene, o-dichlorobenzene, dimethylsulfoxide, γ-butyrolactone, etc., are exemplified. As a supporting electrolyte which is used in the electrolysis solution, a supporting salt comprising a combination of; an alkali metal iron such as lithium ion, potassium ion, sodium ion, etc.; a cation such as a quaternary ammonium ion; and an anion such as a perchlorate ion, boron tetrafluoride ion, phosphorus hexafluoride ion, halogen atom ion, arsenic hexafluoride ion, antimony hexafluoride ion, sulfate ion, hydrogen sulfate ion etc.; is exemplified and preferably added into the electrolysis solution.

As an electrolysis solution, ionic liquids including alkyl imidazolium salts, alkyl pyridinium salts, etc. can be used. As an electrode material, platinum, gold, nickel, ITO, etc. can be used.

The novel polymer of the present invention represented by the formula (V) itself has a high planarity, thus exhibits high self-accumulating characteristics and forms a precisely-layered structure. It also exhibits higher solubility in solvent and better processability, and can be preferably used as a conductive material when compared to that of poly (3,4-ethylene dioxythiophene) (PEDOT).

Examples of the present invention will be described below.

Example 1

Into a 500 ml three-necked flask (reaction container) with thermometer and dropping funnel, 7.72 g (48.8 mmol) of 2-(4-methoxythiophene-3-yl)ethane-1-ol represented by the formula (VI-A) shown below, 11.58 g (146 mmol) of pyridine, and 135 ml of methylene chloride were transferred. The reaction container (flask) was cooled in an ice bath, then 50 ml of methylene chloride containing 18.6 g (97.6 mmol) of p-toluene sulfonic chloride was added dropwise over a period of 10 minutes, then the ice bath was removed from the flask. The reaction solution was stirred at room temperature for a period of 1.5 hours. After the reaction was completed, 100 ml of water was added to separate the organic layer from the water layer. The organic layer was washed twice each with 100 ml of water, then washed twice with saturated aqueous sodium hydrogen carbonate and then dried over anhydrous sodium sulfate. Then it was condensed under a reduced pressure, thereby obtaining a crude product. This crude product was purified using silica gel column chromatography to obtain p-toluene sulfonic acid-2-(4-methoxythiophene-3-yl) ethyl ester (10.5 g, 33.6 mmol, yield 68.9%), a thiophene derivative represented by the formula (IV-A) having properties described below. The chemical equation (X-A) is shown below.

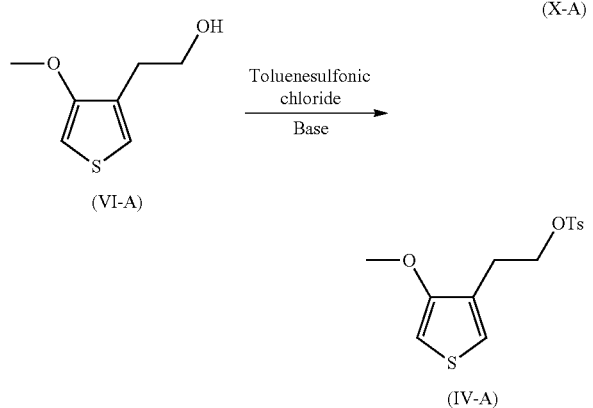

$^1$H-NMR (270 MHz, CDCl$_3$, TMS) σ: 7.71 (d, 2H, J=8.1 Hz), 7.30 (d, 2H, J=8.1 Hz), 6.89 (d, 1H, J=3.0 Hz), 6.11 (d, 1H, J=3.0 Hz), 4.20 (t, 2H, J=7.0 Hz), 3.71 (s, 3H), 2.85 (t, 2H, J=7.0 Hz), 2.44 (s, 3H)

Example 2

Into a 200 ml three-necked flask (reaction container) with thermometer and dropping funnel, 8.61 g (27.6 mmol) of p-toluene sulfonic acid-2-(4-methoxythiophene-3-yl)ethyl ester represented by the formula (IV-A), 2.20 g (28.9 mmol) of thiourea, 40 ml of ethanol and 13.5 ml of water were transferred. The reaction container was heated to 100° C., and then 10 ml of water containing 1.25 g (31.3 mmol) of sodium hydroxide was added dropwise and stirred for a period of 2 hours. After the reaction was completed, 100 ml of toluene and 20 ml of saturated saline were added to separate the organic layer from the water layer. The organic layer was washed twice each with 20 ml of saturated saline water, dried over anhydrous sodium sulfate and then condensed under a reduced pressure, thereby obtaining a crude product. The crude product was purified using silica gel column chromatography. 2-(4-methoxythiophene-3-yl) ethane-1-thiol (2.86 g, 16.4 mmol, 59.5%) represented by the formula (III-A) was obtained. Chemical reaction equation (XI-A) is shown below.

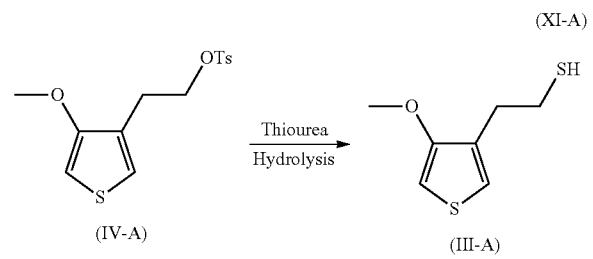

$^1$H-NMR (270 MHz, CDCl$_3$, TMS) σ: 6.92 (d, 1H, J=3.5 Hz), 6.19 (d, 1H, J=3.5 Hz), 3.81 (s, 3H), 2.77 (m, 4H), 1.41 (t, 1H, J=8.1 Hz)

Example 3

Into a 500 ml three-necked flask (reaction container) with thermometer, 2.86 g (16.4 mmol) of 2-(4-methoxythiophene-3-yl)ethane-1-thiol represented by the formula (III-A), 227 mg (1.64 mmol) of sodium hydrogensulfate monohydrate and 200 ml of xylene were transferred. The reaction container was heated to 140° C. and stirred for a period of 40 hours. After the reaction was completed, 100 ml of water was added to separate the organic layer from the water layer. The organic layer was washed twice each with 100 ml of water, dried over anhydrous sodium sulfate, and then condensed under a reduced pressure, thereby obtaining a crude product. The crude product was purified using silica gel column chromatography. 2,3-dihydro-thieno[3,4-b]thiophene (1.01 g, 7.10 mmol, 43.3%) represented by the formula (II-A) having properties described below. The chemical reaction equation (XII-A) is shown below.

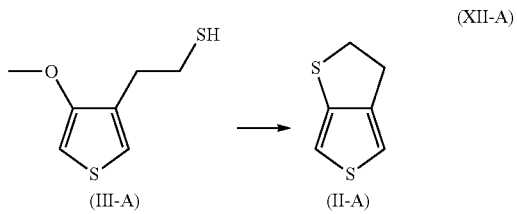

$^1$H-NMR (270 MHz, CDCl$_3$, TMS) σ: 6.84 (d-t, 1H, J=1.4 Hz, 2.4 Hz), 6.62 (d, 1H, J=2.7 Hz), 3.69 (t, 2H, J=7.3 Hz), 3.00 (d-t, 2H, J=1.4 Hz, 7.3 Hz)

Example 4

Into an electrolyzer in which an anode with ITO film-attached glass plate (surface resistance value: 10Ω/□), a platinum cathode and a silver/silver perchlorate reference electrode (10 mM acetonitrile solution) were disposed, 10 ml of 10 mM tetrabutylammonium perchlorate/acetonitrile solution was added and 142 mg (1.00 mmol) of 2,3-dihydro-thieno[3,4-b]thiophene represented by the formula (II-A) was dissolved, and then nitrogen purge was applied. To each electrode of the electrolyzer, a potentiostat/galvanostat HAB-151 (produced by Hokuto Denko Co.) was connected. Electropolymerization was carried out by applying a 0.9V constant potential in potentiostat mode. A black-colored polymer (V-A) was generated on the anode. The reaction equation (XIII-A) is shown below.

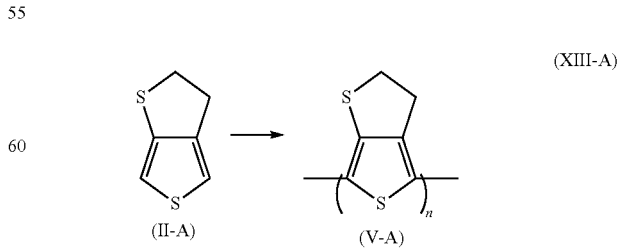

The generated film was washed with dehydrated acetonitrile, and then dried. Electric conductivity was measured using a four-terminal method. The obtained value was 12 S/cm. The result showed that the polymer of the present invention was an excellent conductive material. A neutral state polymer, which was prepared by applying a constant potential of –0.5V, was soluble in an organic solvent such as chloroform, methylene chloride, ethyl acetate, acetone, toluene, tetrahydrofuran, etc., showing that it had a good processability.

Example 5

Into a 500 ml three-necked flask (reaction container) with thermometer and dropping funnel, 4.54 g (26.4 mmol) of 3-(4-methoxy thiophene-3-yl)-propane-1-ol, represented by the formula (VI-B), 8.79 g (111 mmol) of pyridine and 50 ml of methylene chloride were transferred. The reaction container was cooled in an ice bath, then 10 ml of methylene chloride containing 10.1 g (53.0 mmol) of p-toluene sulfonic chloride was added dropwise over a period of 5 minutes, then the ice bath was removed from the flask. The reaction solution was stirred at room temperature for a period of 3.0 hours. After the reaction was completed, 100 ml of water was added to separate the organic layer from the water layer. The organic layer was washed twice each with 100 ml of water, then washed with saturated aqueous sodium hydrogen carbonate, and then dried over anhydrous sodium sulfate. Then it was condensed under reduced pressure, thereby obtaining a crude product. This crude product was purified using silica gel column chromatography to obtain p-toluene sulfonic acid-3-(4-methoxythiophene-3-yl) propyl (681 mg, 20.9 mmol, yield 79.0%) having properties described below. The chemical reaction equation (X-B) is shown below.

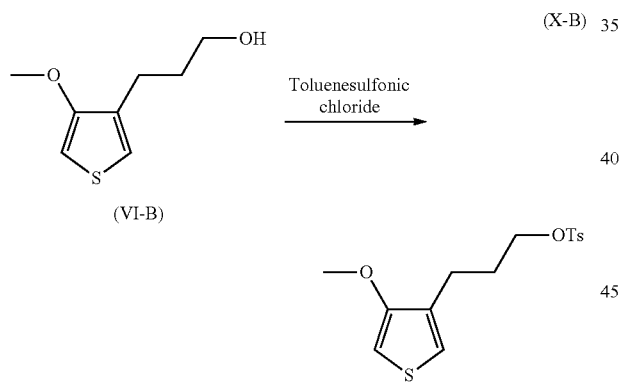

$^1$H-NMR (270 MHz, CDCl$_3$, TMS) σ: 7.78 (m, 2H), 7.33 (d, 2H, 8.4 Hz), 6.71 (d, 1H, J=3.5 Hz), 6.15 (d, 1H, J=3.5 Hz), 4.03 (t, 2H, J=6.2 Hz), 3.77 (s, 3H), 2.52 (d, 2H, J=6.2 Hz), 2.45 (s, 3H), 1.93 (m, 2H)

Example 6

Into a 200 ml three-necked flask (reaction container) with thermometer and dropping funnel, 6.81 g (20.9 mmol) of p-toluene sulfonic acid-3-(4-methoxythiophene-3-yl) propyl ester represented by the formula (IV-B), 1.67 g (21.9 mmol) of thiourea, 30 ml of ethanol and 10 ml of water were transferred, and was heated to 100° C. then 10 ml of water containing 1.25 g (31.3 mmol) of sodium hydroxyde was added dropwise, then stirred for a period of 2 hours. After the reaction was completed, 100 ml of toluene and 20 ml of saturated saline were added to separate the organic layer from the water layer. The organic layer was washed twice each with 20 ml of the saturated saline, and then dried over anhydrous sodium sulfate. Then it was condensed under a reduced pressure, thereby obtaining a crude product. This crude product was purified using silica gel column chromatography to obtain 3-(4-methoxythiophene-3-yl) propane-1-thiol (2.47 g, 13.1 mmol, 62.7%) represented by the formula (III-B) having properties shown below. The chemical reaction equation (XI-B) was shown below.

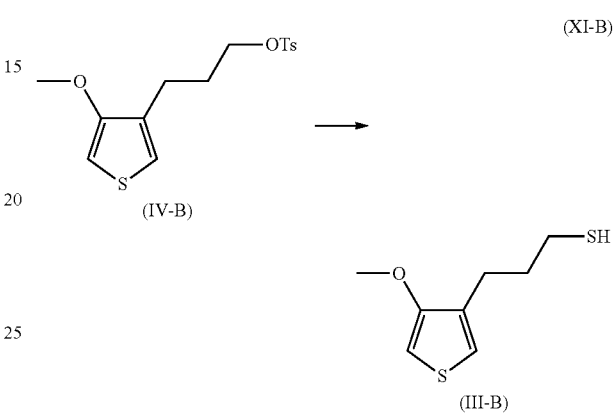

$^1$H-NMR (270 MHz, CDCl$_3$, TMS), σ: 6.84 (d, 1H, J=3.5 Hz), 6.18 (d, 1H, J=3.5 Hz), 3.81 (s, 3H), 2.57 (m, 4H), 1.91 (m, 2H), 1.38 (t, 1H, J=8.1 Hz)

Example 7

Into a 500 ml three-necked flask (reaction container) with thermometer, 2.47 g (13.1 mmol) of 3-(4-methoxythiophene-3-yl) propane-1-thiol represented by the chemical formula (III-B), 320 mg (2.32 mmol) of sodium hydrogen sulfate monohydrate and 100 ml of toluene were transferred and heated to 110° C., then stirred for a period of 8 hours. After the reaction was completed, 100 ml of water was added to separate the organic layer from the water layer. The organic layer was washed twice each with 100 ml of water, and then dried over anhydrous sodium sulfate. Then it was condensed under a reduced pressure, thereby obtaining a crude product. This crude product was purified using silica gel column chromatography to obtain 3,4-dihydro-2H-thieno[3,4-b]thiopyran (1.68 g, 10.8 mmol, 82.4%) represented by the formula (II-B) having properties shown below. The chemical reaction equation (XII-B) is shown below.

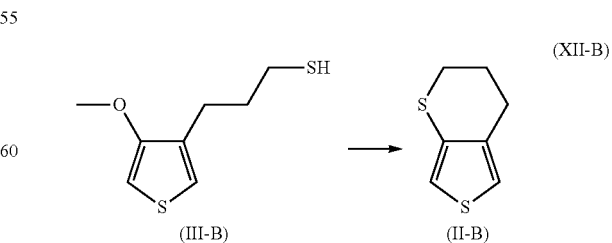

$^1$H-NMR (270 MHz, CDCl$_3$, TMS), σ: 6.95 (m, 1H), 6.77 (d, 1H, J=3.0 Hz), 3.00 (m, 2H), 2.83 (m, 2H), 2.10 (m, 2H)

Example 8

Into an electrolyzer in which an anode with ITO film-attached glass plate (surface resistance value: 10Ω/□), a platinum cathode and a silver/silver perchlorate reference electrode (100 mM acetonitrile solution) were disposed, 10 ml of 100 mM tetrabutylammonium perchlorate/acetonitrile solution was added, and 156 mg (1.00 mmol) of 3,4-dihydro-2H-thieno[3,4-b]thiopyran represented by the formula (II-B) was dissolved. And then nitrogen purge was applied. To each electrode of the electrolyzer, a potentiostat/galvanostat HAB-151 (produced by Hokuto Denko Co.) was connected. Electropolymerization was carried out by applying a 1.2V constant potential in potentiostat mode. A film-like black-colored polymer (V-B) was generated on the anode. The chemical reaction equation (XIII-B) is shown below.

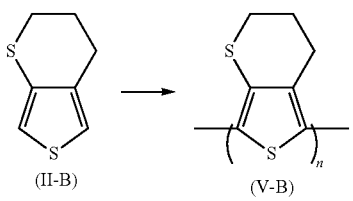
(XIII-B)
(II-B)    (V-B)

The generated film was washed with dehydrated acetonitrile, and then dried. Electric conductivity was measured using a four-terminal method. The obtained value was 15 S/cm. The result showed that the polymer of the present invention was an excellent conductive material. A neutral state polymer, which was prepared by applying a constant potential of −0.5V, was soluble in an organic solvent such as chloroform, methylene chloride, ethyl acetate, acetone, toluene, tetrahydrofuran, etc., showing that it had a good processability.

Comparative Example

In Example 4, chemical reactions and post proceedings were carried out in the same manner as described in Example 4, except that 144 mg (1.00 mmol) of 3-methylmercapto-4-methylthiophene was used instead of 142 mg (1.00 mmol) of 2,3-dihydro-thieno[3,4-b]thiophene. The generated film was washed with dehydrated acetonitrile, and then dried. Electric conductivity was measured using a four-terminal method. The obtained value was $3.0 \times 10^{-2}$ S/cm.

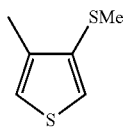
(VIII)

What is claimed is:

1. A thiophene derivative having the chemical structure of formula A or B:

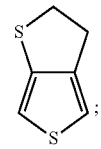
A

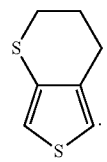
B

2. A method for producing the thiophene derivative of claim 1, comprising a step of subjecting a thiophene derivative represented by chemical formula (III) shown below to an intramolecular cyclization reaction:

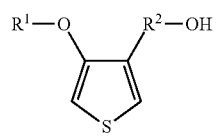
(III)

where:
R$^1$ is an alkyl group having a carbon number of 1 to 10 and optionally having a substituent; and
R$^2$ is an alkyl group having a carbon on number of 2 to 3.

3. A polymer having a constitutional unit of a bicyclic hetero ring skeleton represented by chemical formula A or B:

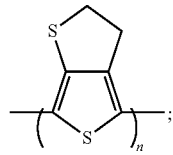
A

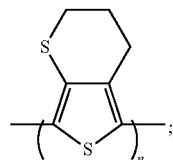
B wherein n is an integer of 2 or more.

4. A composition comprising the polymer of claim 3 and a dopant.

* * * * *